United States Patent [19]
Nelson

[11] Patent Number: 5,708,366
[45] Date of Patent: Jan. 13, 1998

[54] MICROWAVE MOISTURE/YIELD MONITOR WITH CALIBRATION ON-THE-GO

[75] Inventor: George F. Nelson, Coon Rapids, Minn.

[73] Assignee: New Holland North America, Inc., New Holland, Pa.

[21] Appl. No.: 744,250

[22] Filed: Nov. 5, 1996

[51] Int. Cl.⁶ .................................................. G01R 27/04
[52] U.S. Cl. ........................ 324/640; 324/637; 324/601
[58] Field of Search ............................... 324/601, 637, 324/639, 640; 73/61.44, 61.42, 61.43

[56] References Cited

U.S. PATENT DOCUMENTS

| | | | |
|---|---|---|---|
| 3,644,826 | 2/1972 | Cornetet, Jr. | 324/640 |
| 5,001,434 | 3/1991 | Marrelli et al. | 324/640 |
| 5,103,181 | 4/1992 | Gaisford | 324/640 |
| 5,576,974 | 11/1996 | Marrelli et al. | 324/640 |
| 5,644,244 | 7/1997 | Marrelli et al. | 324/640 |

OTHER PUBLICATIONS

IEEE Transactions on Instrumentation and Measurement, vol. 41, No. 1, pp. 111–115, Feb. 1992.
Sensors, Sept. 1992, pp. 68–74.
Canadian Agricultural Engineering, vol. 34, No. 4, pp. 327–335 (Dec. 1992).

*Primary Examiner*—Maura K. Regan
*Attorney, Agent, or Firm*—Griffin, Butler Whisenhunt & Kurtossy

[57] ABSTRACT

In a grain harvester having apparatus for measuring the moisture content of grain by directing a radio frequency signal along a measurement signal path through the grain and determining the moisture content from the phase shift and attenuation experienced by the measurement signal, calibration apparatus is provided for calibrating the moisture measurement apparatus without interrupting the grain harvesting operation. An attenuator, calibrated to a traceable standard, is selectively inserted into the measurement signal path to produce an expected attenuation of the measurement signal. The actual attenuation resulting from the insertion of the attenuator is compared with the expected attenuation and the difference is used to derive a control voltage for controlling the gain of the measurement signal path.

20 Claims, 2 Drawing Sheets

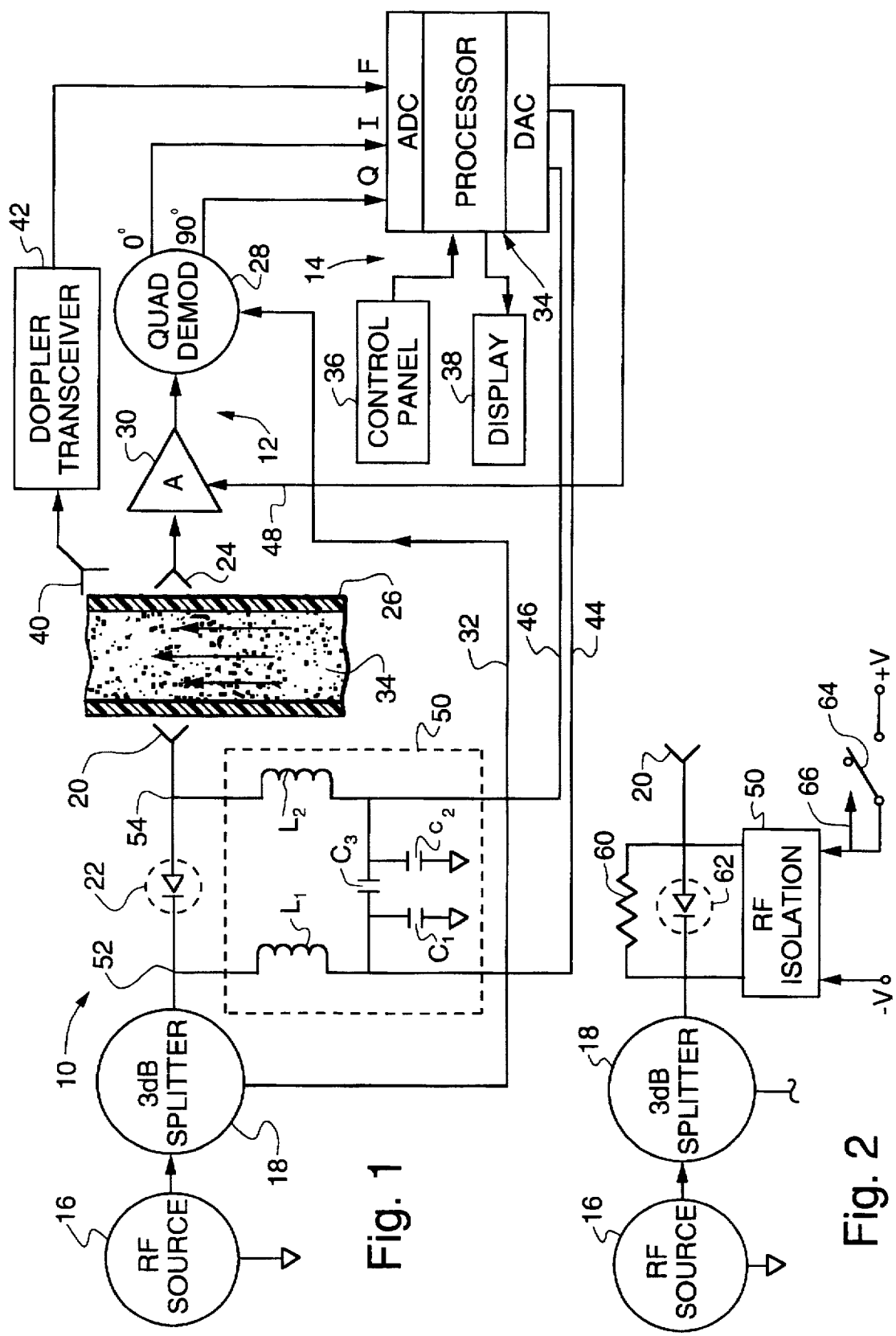

MICROWAVE MOISTURE/YIELD MONITOR WITH CALIBRATION ON-THE-GO

RELATED APPLICATIONS

This application is related to my copending application Ser. No. 08/744,217, entitled Yield/Moisture Monitor Grain Simulator, filed concurrently herewith and assigned to the same assignee as the present application.

FIELD OF THE INVENTION

The present invention relates to a method and apparatus for calibrating moisture/yield monitors of the type used in grain harvesters to measure grain moisture content and crop yield. The invention provides a method and apparatus for calibrating a moisture/yield monitor on-the-go, that is, without interruption of the harvesting operation. The calibration employs an RF attenuator traceable to the National Institute of Standards and Technology hence the moisture measurement of grain is a traceable absolute measurement.

BACKGROUND OF THE INVENTION

It is known that the moisture content of grain and its bulk density may be determined by transmitting an RF signal in the low GHz frequency range through the grain and determining the change in magnitude and phase of the transmitted signal resulting from its passage through the grain. The change in magnitude (attenuation) results primarily from the moisture in the kernels of grain whereas the phase shift is dependent on the bulk density of the grain and, to a lesser extent, on its moisture content. Knowing the moisture content and bulk density of the grain, and by measuring the rate of grain flow through the harvester, the total crop yield may be determined.

It is obviously important to a grower to know his crop yield. The moisture content of the grain is important in that it affects the quality and market value of the grain and its suitability for storage. Therefore, it is desirable that measurements of the moisture content and yield be as accurate as possible. This, in turn, requires accurate calibration of the measurement apparatus.

According to a current method of calibration, microwave apparatus for measuring grain moisture content is calibrated while the apparatus is empty to permit nulling out the imbalance or error in the system resulting from contamination or changes in system components during the measurement interval since the last calibration. This method has several disadvantages. First, since the sensor must be empty the harvesting operation must be interrupted and the accompanying moisture measurement activity suspended. Secondly, if calibration is lost there is no real time record of when the calibration was lost. This means that the accuracy of any measurement made since the last calibration is suspect. Thirdly, the process of nulling out is done by a human operator and thus susceptible to error.

SUMMARY OF THE INVENTION

An object of the present invention is to provide a method and apparatus for calibrating a grain moisture measurement system, the method and apparatus having none of the disadvantages of the prior art.

Another object of the invention is to provide a method and apparatus for calibrating a grain moisture measurement system during the time the system is performing its moisture measurement function.

A further object of the invention is to provide a method and apparatus for calibrating a moisture measurement system in a grain harvester while the grain harvester is harvesting grain from a field.

Still another object of the invention is to provide a measurement system which produces a measurement of the moisture content of grain that is a traceable absolute measurement.

A method of calibration according to the invention comprises electrically inserting into a measurement signal path a resistance having a known attenuation traceable to a standard so as to introduce an expected attenuation in the measurement signal, measuring the actual attenuation, determining the difference between the actual attenuation and the expected attenuation as a result of introduction of the resistance into the measurement signal path, and adjusting the gain of the measurement signal path in accordance with the difference.

According to another aspect of the invention, apparatus for measuring the moisture content of grain comprises a radio frequency signal source, a measurement signal path extending from the signal source through the grain to a receiver circuit, and processing means responsive to output signals from the receiver circuit for determining the moisture content of the grain. The apparatus includes a PIN diode having a calibrated resistance traceable to a standard, the PIN diode being connected in the measurement signal path. A control means selectively biases the diode so that it exhibits no resistance when the apparatus is performing its measurement function but introduces a known resistance into the path during calibration intervals. Introduction of the known resistance into the measurement signal path should produce a known or expected attenuation of the measurement signal if the apparatus is properly calibrated. The processing means determines the difference between the actual and expected attenuations and adjusts the gain of the measurement signal path according to the difference.

Other objects of the invention and the manner of making and using it will be obvious upon consideration of the following description and the accompanying drawings.

BRIEF DESCRIPTION OF DRAWINGS

FIG. 1 illustrates a first embodiment of an apparatus for measuring the moisture content of grain, the apparatus including a PIN diode selectively biased by a processor to introduce a known value of resistance into a measurement signal path for calibration purposes;

FIG. 2 illustrates alternative arrangements for introducing a known resistance into a measurement signal path; and, FIG. 3 illustrates a routine executed by the processor of FIG. 1 to control automatic on-the-go calibration of the apparatus.

DESCRIPTION OF PREFERRED EMBODIMENTS

Figure 3:
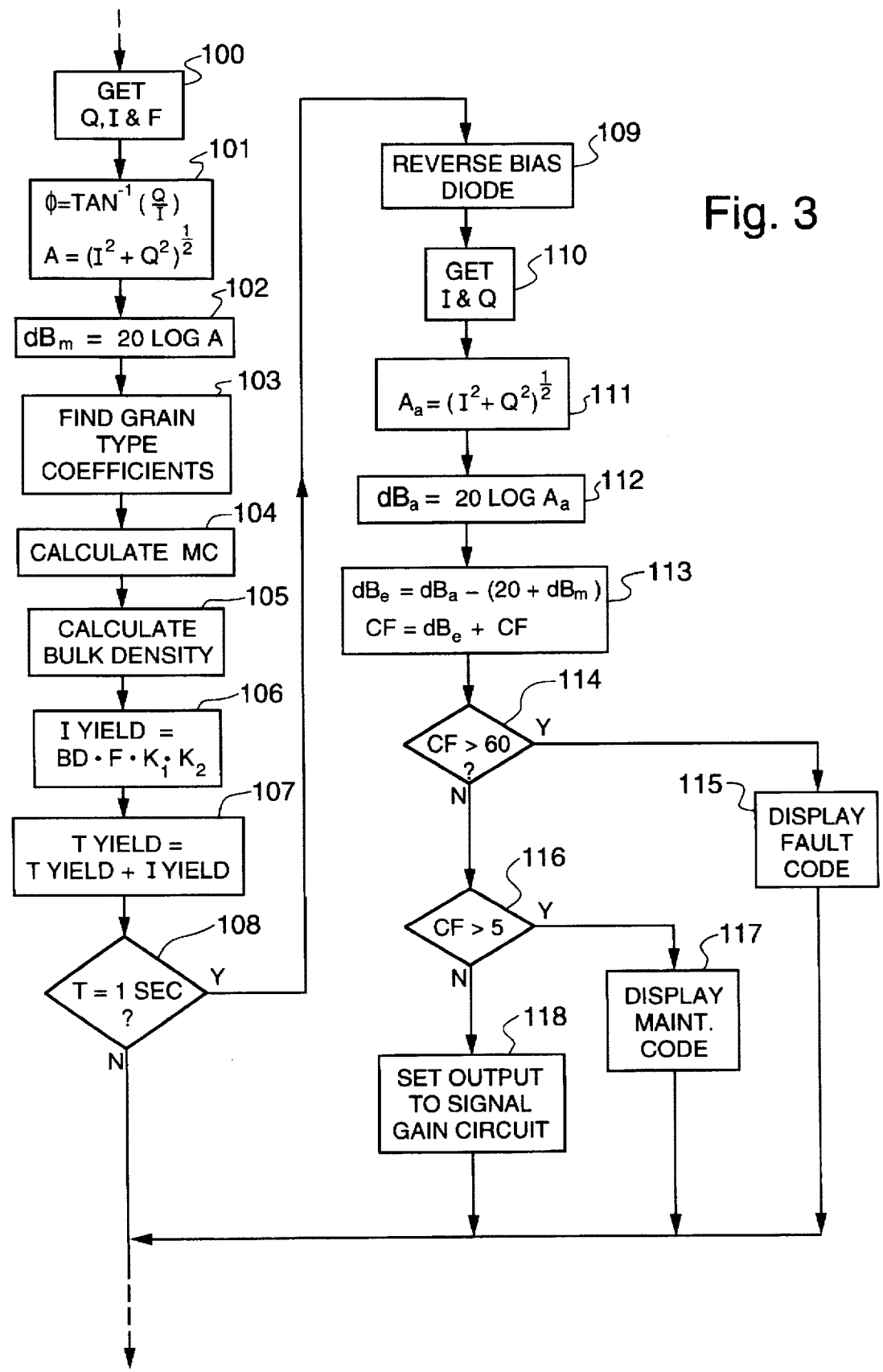

Referring to FIG. 1, an apparatus for measuring the moisture content of grain and determining crop yield comprises an RF transmitting means 10, a receiver circuit means 12 and a controller or processor means 14.

The RF transmitting means 10 comprises an RF source 16 for continuously producing a measurement signal in the frequency range of about 1–10 GHz, a signal splitter 18, and a transmit antenna 20. The measurement signal output of RF source 16 is connected to the signal splitter 18 and one output of the signal splitter is applied to the transmit antenna 20 through a PIN diode 22.

A receive antenna 24 drives the receiver circuit means 12. The antennas 20, 24 are disposed on opposite sides of a closed conveyor chute 26 which comprises a part of the grain flow path in a grain harvester. The chute 26 is made of a low dielectric plastic material, or is provided with windows of such a material, so as to have minimal effect on the RF signals as they pass through it. Preferably, an interrupted flyte auger (not shown) moves the grain through chute 26. As is known in the art, the auger flyte is interrupted so that grain may accumulate and completely fill chute 26 in the region between antennas 20, 24, thereby providing a more uniform density of the grain through which the signal from transmit antenna 20 passes.

The receiver circuit means 12 includes a quadrature demodulator 28 and, as illustrated in FIG. 1, a gain control means such as a controllable amplifier 30 connected between the receive antenna and one input of the demodulator. The output of signal splitter 18 is connected to a second input of the demodulator via a lead 32 so as to apply to the demodulator a reference signal which is in phase with the signal applied to transmit antenna 20.

The demodulator may, for example, be a type MIQ64M5-2 quadrature demodulator commercially available from Magnum Microwave Corporation, San Jose Calif. The demodulator produces two time varying output voltages I and Q where I and Q represent the magnitude of the output signal from amplifier 30 measured at 0° and 90° of the reference signal on lead 32. The signals I and Q provide an indication of the attenuation and phase shift of a measurement signal as the signal is propagated over the measurement signal path extending from splitter 18 to antenna 20, through grain 34 in chute 26, and from the antenna 24 to demodulator 28. The attenuation A of the measurement signal is $(I^2+Q^2)^{1/2}$ volts and the phase $\emptyset$ is $\tan^{-1}$ (Q/I) degrees.

The controller or signal processor means 14 comprises a processor 34, an operator's control panel 36 and an alphanumeric display 38. The control panel and display are located near the operator's seat in the harvester so that the operator may conveniently enter control commands or data into the processor and observe data and messages generated by the processor.

The processor 34 may be a conventional programmable microprocessor having ROM, RAM and EEPROM memories as well as analog to digital (ADC) and digital to analog (DAC) conversion circuits.

In order to determine crop yield, it is necessary to know the speed of grain flow through the chute 26. The means for sensing grain speed comprises a doppler transmit/receive antenna 40 connected to a doppler transceiver 42. The output signal F from transceiver 42 and the output signals I and Q from demodulator 28 are all applied to the ADC circuits of the processor.

As subsequently explained, the processor 34 operates during measurement intervals to repetitively sample the signals Q, I and F. From I, Q and F the processor determines grain moisture content, bulk density and yield. Intermittently, and while grain may be flowing through chute 26, the processor executes a calibrate routine and, if adjustment is necessary, sets the control voltage applied to the gain circuit 30 over lead 48 during subsequent measurement intervals. For this purpose, the DAC circuits of processor 34 produce output signals on leads 44, 46 and 48.

The signals on leads 44 and 46 are applied through an RF isolation circuit 50 to two junctions 52, 54. Processor 34 with its DAC circuits comprise a means for selectively applying a bias current to the PIN diode 22. The diode may, for example, be a Hewlett-Packard type 5082-3340 PIN diode attenuator with calibration traceable to the National Institute of Standards and Technology. When zero or reverse bias is applied to the diode it exhibits a very high resistance, introducing a known attenuation into the measurement signal path. When a forward bias is applied to the diode its resistance drops to practically zero, actually to a value less than one ohm.

The RF isolation circuit 50 serves to isolate the RF output of splitter 18 from the processor 34. The inductances $L_1$, $L_2$ serve as chokes to block the RF signal. Capacitors $C_1$, $C_2$ and $C_3$ act to filter any of the RF signal passing through the inductances to prevent it from reaching the processor.

Assume that the apparatus of FIG. 1 is in a measurement mode, that is, not in the process of being calibrated. The processor 34 produces signals on leads 44 and 46 to forward bias diode 22 so that it introduces no resistance or loss into the measurement signal path. The continuous output signal from source 16 is split by splitter 18 and applied to transmit antenna 20 and demodulator 28.

The measurement signal is transmitted through the grain flowing in chute 26 where it is attenuated and shifted in phase to a degree dependent on the internal moisture content of the kernels of grain and the density of the grain. The phase shifted and attenuated measurement signal is amplified by gain control means 30 and applied to demodulator 28 which in turn produces the time varying voltage signals I and Q that are applied to the ADC circuits of processor 34.

As will be evident from the following description, the diode 22 and gain control means 30 do not have to be located in the circuit positions shown in FIG. 1. Either of these elements may be located anywhere in the measurement signal path downstream of the signal source 16 and upstream of demodulator 28.

FIG. 3 illustrates a routine executed by processor 34 to calculate grain moisture content and yield and, in accordance with the present invention, calculate a correction factor for calibrating or adjusting the gain of the measurement signal path. The routine is executed periodically at intervals of 10 ms but his interval is not critical. During each execution of the routine steps 100–108 are carried out to calculate moisture content and yield. In addition at intervals of, for example 1 sec, steps 109–118 are carried out to develop a calibration factor for adjusting the gain in the measurement signal path, or produce a message for the operator regarding the condition of the measurement system.

At step 100, the microprocessor gets from the ADC circuits digitized values corresponding to the magnitudes of the analog signals Q, I and F. Step 101 computes the phase shift $\emptyset$ and attenuation A imposed on the measurement signal as it passes over the measurement signal path and through the grain in chute 26. The phase shift $\emptyset$ is computed according to the equation $\emptyset$ (in degrees) $=\tan^{-1}$ (Q/I) and the measured attenuation is computed according to the equation A (in volts)$=(I^2+Q^2)^{1/2}$.

Step 102 converts the attenuation to an equivalent decibel loss $dB_m$.

Step 103 obtains from the processor memory the grain coefficients required to calculate grain moisture content. In this regard, the kernels of different grains such as wheat, corn, etc. and different varieties of the same grain, such as soft and hard red winter wheat, exhibit different physical characteristics which must be taken into account in determining the moisture content of the grain. A look-up table is provided in the non-volatile memory in processor 34 and this table stores constants which are used in computing the moisture content. Prior to initiation of a harvesting operation, the operator enters through control panel 36 an indication of the type/variety of grain to be harvested. At step 103, this indication is used to address the look-up table to obtain the constants to be used in calculating the moisture content and bulk density.

At steps 104 and 105, the processor 34 calculates the moisture content and the bulk density using the measured values of attenuation and phase shift and the appropriate constants obtained from the look-up table. The prior art discloses many experimentally developed equations for computing grain moisture content and bulk density from the measured phase shift and attenuation imparted to an RF signal as it passes through grain. For example, the calculations of moisture content and bulk density may be carried out according to the equations of Kraszewski and Nelson as set forth in Canadian Agricultural Engineering, Vol. 34, No. 4, pgs. 327–335(1992). The calculations of moisture content and bulk density are not, per se, a part of the present invention and need not be discussed further.

Step 106 determines the incremental yield (IYIELD). That is, at step 106 the processor determines the crop yield in the interval of time elapsing between consecutive executions of step 106. IYIELD=BD×F×$K_1$×$K_2$ where BD is the bulk density calculated at step 105, F is the velocity of grain flow through chute 26, $K_1$ is the cross-sectional area of the interior of chute 26 and $K_2$ is the time between consecutive executions of step 106.

At step 107, IYIELD is added to total yield (TYIELD). The value in TYIELD represents the total crop yield or total crop processed since the start of the harvesting operation.

In summary, steps 100–107 sample and convert the analog output signals Q, I and F from demodulator 28 and transceiver 42 to digital values, determine the phase shift ∅ and attenuation A of the measurement signal, compute the moisture content and bulk density of the grain, and from the bulk density determine the total crop yield.

According to the routine illustrated in FIG. 3, calibration is carried out once each second. A timer (T) tolls the one-second intervals. T is incremented by 10 ms each time step 108 is executed and the value in T is tested to determine if it represents one second. If one second has not passed the processor bypasses calibration steps 109–118 and exits the routine.

On the other hand, if timer T holds a value representing one second when it is tested at step 108, the timer is reset to begin tolling another one-second interval and the processor 34 advances to step 109 to perform a calibration.

The interval of one second is not critical. Other intervals may be used. It is possible to eliminate step 108 entirely so that the processor performs a calibration following each measurement. In this case, the step 108 is eliminated and the routine moves from step 107 directly to step 109

The processor 34 carries out a calibration by reverse biasing PIN diode 22, measuring the actual attenuation of the measurement signal with the resistance of the diode in the measurement signal path, and determining the difference between the actual attenuation and the expected attenuation. Assuming the PIN diode 22 is a 20 dB attenuator, the expected attenuation is assumed to be 20 dB greater than the attenuation determined at steps 100–102 immediately prior to insertion of the diode resistance into the measurement signal path. Although grain may, or may not be flowing, this assumption is quite accurate because the measurement of attenuation for calibration purposes always takes place in a matter of microseconds after steps 100–102 are executed.

At step 109, the processor sets outputs so that the DAC circuits produce output signals on leads 44, 46 to reverse bias PIN diode 22. The resistance of the PIN diode increases to a known value thus introducing into the measurement signal path a resistance which should produce a known expected attenuation of the measurement signal if the gain of the measurement signal path is properly adjusted.

To determine the actual attenuation resulting from insertion of the PIN diode resistance into the measuring path, the processor 34 samples the signals I and Q (step 110) while the PIN diode is still reverse biased, and from I and Q computes the actual attenuation $A_a$ (step 111).

Processor 34 next determines the difference between the expected attenuation and the actual attenuation resulting from insertion of the PIN diode resistance into the measurement signal path. The actual attenuation value $A_a$ calculated at step 111 is expressed in volts and this value is converted (step 112) to the equivalent actual loss $dB_a$ in decibels. The actual loss $dB_a$ should be 20 dB greater than the loss $dB_m$ determined at step 102. Therefore, at step 113 the processor subtracts from the actual attenuation $dB_a$ the sum of 20 dB plus the attenuation $dB_m$ to obtain the difference $dB_e$ between the actual attenuation and the expected attenuation resulting from insertion of the diode resistance into the measurement signal path.

The value $dB_e$ is used to adjust the gain of the measurement signal path so that, assuming no further changes in the measurement signal path, the value $dB_e$ will be zero the next time a calibration is carried out. However, the value $dB_e$ cannot be used directly to set the output signal on lead 48 to control the gain. At the time the signal samples are taken at steps 100 and 110, the processor 34 is already applying a gain adjustment signal to amplifier 30 as a result of prior calibrations which developed prior difference values $dB_e$. A correction factor CF, representing the algebraic sum of these prior difference values is stored in memory. Step 113 adds $dB_e$ to CF and the result is saved for use during the next calibration.

The value CF is used to set the magnitude of the gain adjustment signal applied to amplifier 30 over lead 48. However, before the gain adjustment signal is set, the value CF is checked to determine its magnitude. At step 114, the value of CF is checked to see if it represents an attenuation greater than 60. If so, it is probably a result of a circuit failure. At step 115 the processor sets an output message which is applied to display 38 to inform the operator. An audible alarm may also be sounded to call the operator's attention to the error.

If step 114 determines that CF is less than 60, step 116 is executed to determine if CF is greater than 5. If CF is greater than 5, it is an indication that some maintenance should be performed such as cleaning dirt/moisture from the region between the antennas 20, 24. In this case an appropriate message is sent to display 38 (step 117) and an audible alert is sounded.

If step 116 determines that CF is no greater than 5, the value of CF is used (step 118) to set an output signal to the amplifier 30 to thereby adjust the gain of the measurement signal path. CF, which is in terms of decibels, is used to access a conversion table. The resulting output value from the conversion table is converted to an analog signal by the ADC circuits and the analog signal is applied over lead 48 to the amplifier.

The resistance of PIN diode 22 may be removed from the measurement signal path at any time after I and Q are sampled at step 110 by placing signals on leads 44, 46 to forward bias the diode.

Although FIG. 1 illustrates the invention in a specific moisture/yield monitoring system, it should be understood the invention is equally suitable for use in other systems such as, for example, those systems wherein the signal from the receive antenna 24 is split and applied in parallel to a phase comparator and an amplitude comparator for comparison with the reference signal.

The invention may also be implemented in different ways as illustrated in FIG. 2. For example an attenuator 60, calibrated to a traceable standard may be connected in the measurement signal path and selectively switched into, or out of, the path by a suitable switching means 62 illustrated as a PIN diode. When the diode is forward biased, the measurement signal flows through the diode and the attenuator is removed from the signal path. When the diode is reverse biased it blocks the measurement signal path and the attenuator is electrically inserted into the signal path.

Although illustrated as a PIN diode, switching means 62 may be a pair of electronic switches or even a manual switch with contacts in series with attenuator 60.

The bias voltage for biasing the PIN diode 22 or 62 need not come from the processor 34. A manual switch 64 may be provided for selectively connecting a source of bias voltage to the diode. Output lead 66 from the switch may be connected to the processor 34 and, in FIG. 3, step 108 is replaced by a step in which actuation of switch 64 is sensed.

Other modifications and substitutions may be made in the preferred embodiment without departing from the spirit and scope of the invention a defined by the appended claims.

I claim:

1. Apparatus for measuring the moisture content of grain comprising:

a radio frequency signal source for producing a measurement signal;

a measurement signal path including, a transmit antenna responsive to said signal source for transmitting said measurement signal through the grain, a gain control means for controlling the magnitude of said measurement signal as said measurement signal moves along said measurement signal path, a receive antenna responsive to said measurement signal after it has passed through the grain, and receiver circuit means responsive to said receive antenna for producing signals indicative of the attenuation and phase shift of said measurement signal resulting from the passage of the measurement signal through the grain;

processor means responsive to said signals indicative of the attenuation and phase shift for determining the attenuation of said measurement signal and the moisture content of the grain;

means for electrically introducing into said measurement signal path a resistance having a known attenuation to cause an expected attenuation of said measurement signal;

said processor means including means for determining the difference between an expected and an actual attenuation of said measurement signal as a result of insertion of said resistance into said measurement signal path; and, means for adjusting said gain control means according to said difference.

2. Apparatus as claimed in claim 1 wherein said gain control means is connected in said measurement signal path downstream of said receive antenna.

3. Apparatus as claimed in claim 1 wherein said means for electrically introducing into said measuring signal path said resistance of known value comprises:

a PIN diode connected in said measurement signal path, said PIN diode having a resistance to bias voltage relationship calibrated to a traceable standard; and, means for selectively applying to said PIN diode a bias voltage having a first value whereby said PIN diode exhibits no resistance and a bias voltage having a second value whereby said PIN diode exhibits a known resistance greater than zero.

4. Apparatus as claimed in claim 3 wherein said means for selectively applying the bias voltage having said first value and the bias voltage having the second value comprises digital to analog conversion means responsive to said processor means.

5. Apparatus as claimed in claim 3 wherein said PIN diode is connected in said measurement signal path upstream of said transmit antenna.

6. Apparatus as claimed in claim 5 wherein said gain control means is connected in said measurement signal path downstream of said receive antenna.

7. Apparatus as claimed in claim 1 wherein said processor means includes means for sampling the signals produced by said receiver circuit means before and after said resistance is introduced into said measurement signal path to thereby determine the attenuation of said measurement signal before and after said resistance is introduced into said measurement signal path, said means for determining the difference between the expected and actual attenuation of said measurement signal comprises means for subtracting the sum of said known attenuation and the attenuation determined prior to introducing said resistance into the measurement signal path from the attenuation determined after said resistance is introduced into said measurement signal path.

8. Apparatus as claimed in claim 1, said apparatus being mounted on a grain harvester, said transmit antenna and said receive antenna being mounted on opposite sides of a grain flow path through which harvested grain flows.

9. Apparatus as claimed in claim 8 wherein said means for electrically introducing into said measurement signal path a resistance of known value comprises means for intermittently electrically introducing said resistance into said measurement signal path while grain is flowing through said grain flow path.

10. Apparatus as claimed in claim 8 wherein said gain control means is connected in said measurement signal path downstream of said receive antenna.

11. Apparatus as claimed in claim 8 wherein said means for electrically introducing into said measurement signal path said resistance of known value comprises:

a PIN diode connected between said radio frequency signal source and said transmit antenna, said PIN diode having a resistance to bias voltage relationship calibrated to a traceable standard; and, means for selectively applying to said PIN diode a bias voltage having a first value whereby said PIN diode exhibits no resistance and a bias voltage having a second value whereby said PIN diode exhibits a known resistance greater than zero.

12. Apparatus as claimed in claim 11 wherein said PIN diode is connected in said measurement signal path upstream of said transmit antenna.

13. Apparatus as claimed in claim 11 wherein said means for selectively applying the bias voltage having said first value and the bias voltage having said second value comprises digital to analog conversion means responsive to said processor means for applying said bias voltage to said PIN diode.

14. Apparatus as claimed in claim 8 wherein said means for electrically introducing into said measurement signal path said resistance of known value comprises:

a resistor connected between said radio frequency signal source and said transmit antenna, said resistor having a known resistance traceable to a standard;

a PIN diode connected in parallel with said resistor; and, bias means for selectively applying a bias voltage to said PIN diode whereby said PIN diode selectively exhibits no resistance or a very high resistance relative to said resistor.

15. Apparatus as claimed in claim 1 wherein said receiver circuit means comprises a quadrature demodulator connected to said radio frequency signal source and an amplifier connected between said receive antenna and said demodulator, said demodulator producing signals I and Q wherein $\tan^{-1}(Q/I)=\theta$ is the phase shift of the measurement signal and $(I^2+Q^2)^{1/2}=A$ is the attenuation of said measurement signal, said processor means including means responsive to signals I and Q for determining A and $\theta$.

16. Apparatus as claimed in claim 15 wherein said means for adjusting said gain control means comprises digital to analog converter means associated with said processor means for applying a control signal to said gain control means.

17. Apparatus as claimed in claim 9 wherein said receiver circuit means comprises a quadrature demodulator connected to said radio frequency signal source and an amplifier connected between said receive antenna and said demodulator, said demodulator producing signals I and Q wherein $\tan^{-1} Q/I=\theta$ is the phase shift of the measurement signal and $(I_2+Q^2)^{1/2}=A$ is the attenuation of said measurement signal, said processor means including means responsive to signals I and Q for determining A and $\theta$.

18. A method of calibrating an apparatus for measuring the moisture content of grain flowing along a grain flow path in a grain harvester, said apparatus having a radio frequency signal source and a measurement signal path including a transmit antenna responsive to said signal source for transmitting a measurement signal through the flowing grain, a receiver antenna responsive to said measurement signal after it has passed through the grain, receiver circuit means responsive to said receiver antenna for producing signals indicative of the attenuation and phase shift of said measurement signal resulting from the passage of the measurement signal through the grain, gain control means for controlling the gain of said measurement signal path, and processor means responsive to said signals indicative of the attenuation and phase shift for determining the attenuation of said measurement signal, said method comprising :

while grain is flowing along said grain flow path, electrically introducing into the measurement signal path an attenuator of known value to cause an expected attenuation of said measurement signal, determining the difference between the expected attenuation of said measurement signal and the actual attenuation of said measurement signal resulting from the introduction of said attenuator into the measuring signal path, and, adjusting said gain control means in accordance with said difference.

19. A method as claimed in claim 18 wherein the step of intermittently introducing the attenuator of known value into the measurement signal path comprises providing a PIN diode, calibrated to a traceable standard, in said measurement signal path and selectively biasing said PIN diode whereby said PIN diode selectively exhibits no resistance or a known resistance greater than zero.

20. A method as claimed in claim 19 wherein the step of determining the difference between the expected attenuation and the actual attenuation comprises comparing the attenuation of said measurement signal immediately prior to introducing said attenuator of known value into the measurement signal path with the sum of the attenuation of said attenuator and the attenuation of said measurement signal with said attenuator introduced into said measurement path.

\* \* \* \* \*